(12) United States Patent
Yang et al.

(10) Patent No.: US 9,547,165 B2
(45) Date of Patent: Jan. 17, 2017

(54) ENDOSCOPE SYSTEM WITH SINGLE CAMERA FOR CONCURRENT IMAGING AT VISIBLE AND INFRARED WAVELENGTHS

(71) Applicant: REINROTH GMBH, Herbolzheim (DE)

(72) Inventors: Chunxin Yang, San Jose, CA (US); Xing Hui, San Jose, CA (US); Baiyu Wang, San Jose, CA (US); Claudio Immekus, Herbolzheim (DE)

(73) Assignee: REINROTH GMBH, Herbolzheim (DE)

( * ) Notice: Subject to any disclaimer, the term of this patent is extended or adjusted under 35 U.S.C. 154(b) by 151 days.

(21) Appl. No.: 14/473,930

(22) Filed: Aug. 29, 2014

(65) Prior Publication Data

US 2016/0062103 A1 Mar. 3, 2016

(51) Int. Cl.
*A61B 1/05* (2006.01)
*G02B 23/24* (2006.01)
*G01N 21/55* (2014.01)
*G01N 21/64* (2006.01)

(52) U.S. Cl.
CPC ............ *G02B 23/2461* (2013.01); *G01N 21/55* (2013.01); *G01N 21/6456* (2013.01); *G01N 2201/06113* (2013.01); *G01N 2201/08* (2013.01)

(58) Field of Classification Search
CPC ...................... G06T 2207/10068; G02B 23/24; G01N 21/64; G01N 21/55; G01N 2021/6419; A61B 1/05; A61B 5/00; A61B 1/06; A61B 1/042; A61B 1/026

USPC ........................ 250/201.3, 221, 559.4, 208.1, 250/363.01–363.04; 600/157–178, 108, 600/129; 359/353, 634, 9

See application file for complete search history.

(56) References Cited

U.S. PATENT DOCUMENTS

| | | | |
|---|---|---|---|
| 5,864,359 A | 1/1999 | Kazakevich | |
| 5,910,816 A | 6/1999 | Fontenot et al. | |
| 6,293,911 B1 | 9/2001 | Imaizumi et al. | |
| 7,179,222 B2 | 2/2007 | Imaizumi et al. | |
| 8,498,695 B2 | 7/2013 | Westwick et al. | |
| 8,740,779 B2 * | 6/2014 | Yoshida | A61B 1/00091 600/157 |
| 8,773,756 B2 * | 7/2014 | Tesar | G01J 3/36 359/353 |
| 2011/0213252 A1 | 9/2011 | Fulghum et al. | |
| 2011/0270092 A1 | 11/2011 | Kang et al. | |
| 2012/0004508 A1 | 1/2012 | McDowall et al. | |
| 2012/0249771 A1 | 10/2012 | Haisch et al. | |

FOREIGN PATENT DOCUMENTS

WO 2016032729 3/2016

OTHER PUBLICATIONS

PCT/US2015/044326, "International Search Report and Written Opinion", Nov. 12, 2015, 11 pages.

* cited by examiner

*Primary Examiner* — Que T Le
(74) *Attorney, Agent, or Firm* — Kilpatrick Townsend & Stockton LLP

(57) ABSTRACT

A method of operating an endoscopy system includes concurrently illuminating a tissue with NIR excitation light and visible light, imaging the tissue using a single detector, and independently adjusting an intensity of the NIR excitation light and an intensity of the visible light.

18 Claims, 6 Drawing Sheets

ENDOSCOPE SYSTEM WITH SINGLE CAMERA FOR CONCURRENT IMAGING AT VISIBLE AND INFRARED WAVELENGTHS

STATEMENT AS TO RIGHTS TO INVENTIONS MADE UNDER FEDERALLY SPONSORED RESEARCH OR DEVELOPMENT

Not Applicable

BACKGROUND OF THE INVENTION

Medical endoscopes have been widely used in both diagnostic and surgical procedures. A promising technique for detecting a lesion in a living body during endoscopic procedures involves near infrared (NIR) fluorescence imaging, in which NIR light is used to illuminates tissue, exogenously applied fluorophores in the tissue emit fluorescence, and an imaging system captures a fluorescent image. In addition to fluorescence imaging, normal diagnostic and surgical procedures utilize endoscopy with conventional visible light imaging.

Despite the progress made in the field of endoscopy, there is a need in the art for a system incorporating visible light endoscopy and NIR fluorescent endoscopy.

SUMMARY OF THE INVENTION

The present invention relates generally to endoscopy systems. More particularly, embodiments of the present invention relate to an apparatus and method for concurrent imaging of both visible light and NIR fluorescence during endoscopy. In a particular embodiment, an endoscope system with concurrent visible light imaging and NIR fluorescence imaging is provided. The endoscope system disclosed, comprising an endoscope working from visible to NIR spectra, a light source generating independently controllable visible light and NIR excitation light, a single image sensor camera, a controller for image processing and light source control, and a display device. The fluorescence imaging mode starts with an initialization process which adjusts intensity of the NIR excitation light and visible light independently until the brightness of fluorescence image and the contrast between fluorescence image and visible light image are ideal for observation.

According to an embodiment of the present invention, an endoscope system for concurrently imaging at both visible and NIR wavelengths is provided. The endoscope system includes an endoscope operable to transmit both visible and NIR wavelengths and a light source operable to generate visible light and NIR excitation light. An intensity of the visible light is independent of an intensity of the NIR excitation light. The endoscope system also includes a camera having a single image sensor, a controller coupled to the visible light and the NIR excitation light, and a display device.

According to another embodiment of the present invention, a method of operating an endoscopy system is provided. The method includes concurrently illuminating a tissue with NIR excitation light and visible light, imaging the tissue using a single detector, and independently adjusting an intensity of the NIR excitation light and an intensity of the visible light.

According to a specific embodiment of the present invention, a method of initializing an endoscope is provided. The method includes illuminating tissue with NIR excitation light and imaging fluorescent emission from the tissue with a single image sensor. The method also includes adjusting an intensity of the NIR excitation light until a fluorescence image intensity is within a predetermined rage and determining fluorescence active pixels and fluorescence non-active pixels. The method further includes illuminating the tissue with visible light, imaging both the fluorescent emission from the tissue and reflected visible light with the single image sensor, computing a ratio between an average signal value of the fluorescence active pixels and the fluorescence non-active pixels, and adjusting an intensity of the visible light.

In an embodiment, an endoscope system for simultaneous imaging in both the visible and the NIR regions is provided. The endoscope system includes an endoscope with desired image quality over the visible and the NIR spectrum and a light source generating visible light and NIR excitation light. The light source is configured such that intensity of the visible light and the intensity of the NIR excitation light can be independently controlled. The endoscope system also includes a camera with a single image sensor that is operable to capture images and output image signals, a controller capable of controlling visible light and NIR excitation light independently, and a display device. The controller is configured to process the image signals and adjust the light intensity based on image processing.

In a specific embodiment, the camera of the endoscope system includes an optical filter that blocks the excitation light and passes visible light and fluorescence emission. The light source can include a plurality of solid state light sources, each of which is independently controlled. The controller can be further capable of attenuating the intensity of the visible light through optical or electrical approaches.

In another embodiment, a method for simultaneously imaging visible light and NIR fluorescence emission with a single image sensor is provided. The method includes an initialization process that includes illuminating tissue only with NIR excitation light, capturing and imaging fluorescence emission with a single image sensor, and adjusting the intensity of the NIR excitation light until the brightness of the fluorescence image is at a desired level. The method also includes adding visible light with attenuated intensity for illumination, capturing and imaging fluorescence emission and reflected visible light with the single image sensor, and adjusting the intensity of visible light until the contrast between the fluorescence emission and the reflected visible light is at a desired level.

In an embodiment, the method also includes distinguishing fluorescence active pixels and fluorescence non-active pixels by applying a threshold to the fluorescence image when illuminating tissue only with the NIR excitation light. The method can also include determining a ratio between an average signal value of the fluorescence active pixels and an average signal value of the fluorescence non-active pixels when illuminating tissue with both NIR excitation light and visible light.

In a specific embodiment, an endoscope system for simultaneous visible light imaging and NIR fluorescence imaging is provided. The endoscope system includes an endoscope working from visible to NIR spectra, a light source generating independently controllable visible light and NIR excitation light, a single image sensor camera, a controller for image processing and light source control, and a display device. The fluorescence imaging mode starts with an initialization process that adjusts the intensity of the NIR excitation light and the visible light independently until the brightness of fluorescence image and the contrast between the fluorescence image and the visible light image are suitable for observation.

Numerous benefits are achieved by way of the present invention over conventional techniques. For example, embodiments of the present invention provide endoscopy systems that utilize concurrent illumination in both the NIR spectrum and the visible spectrum and imaging in both the fluorescent emission spectrum and the reflected visible spectrum to provide information for medical procedures that is not available using conventional techniques. These and other embodiments of the invention along with many of its advantages and features are described in more detail in conjunction with the text below and attached figures.

DETAILED DESCRIPTION OF SPECIFIC EMBODIMENTS

In NIR fluorescence endoscopy, exogenous fluorophores such as indocyanine green (ICG) can be administered to the patient and will combined with the tissue to be observed. In addition to IGC, other suitable dyes, such as methylene blue can be used as a source of fluorescent emission. Excitation light in the NIR spectrum with wavelengths shorter than the fluorescent emission is used to illuminate the tissue and excites the fluorophores in the tissue. The resulting fluorescence emission is detected at NIR wavelengths longer than the excitation light based on the Stokes shift. The fluorescence quantum yields give the efficiency of the fluorescence process, which is normally low. As a result, the intensity of the fluorescence emission is generally very weak compared to the intensity of the NIR excitation light. Therefore, in order to observe the fluorescence image, an optical filter is utilized to block the NIR excitation light from reaching the sensor.

A CCD or CMOS image sensor typically has a spectral response from 200 nm to 1100 nm, allowing the sensor to capture light for imaging in both the visible and NIR regions. However, the spectral response of an image sensor in the NIR spectrum is only 10%-30% of its peak response in the visible spectrum. Thus embodiments of the present invention, which provide endoscopy incorporating both visible light and NIR fluorescence imaging, utilize control of the intensity of the visible light and the intensity of the NIR excitation light so that the reflected visible light does not overwhelm the image sensor.

Figure 1:
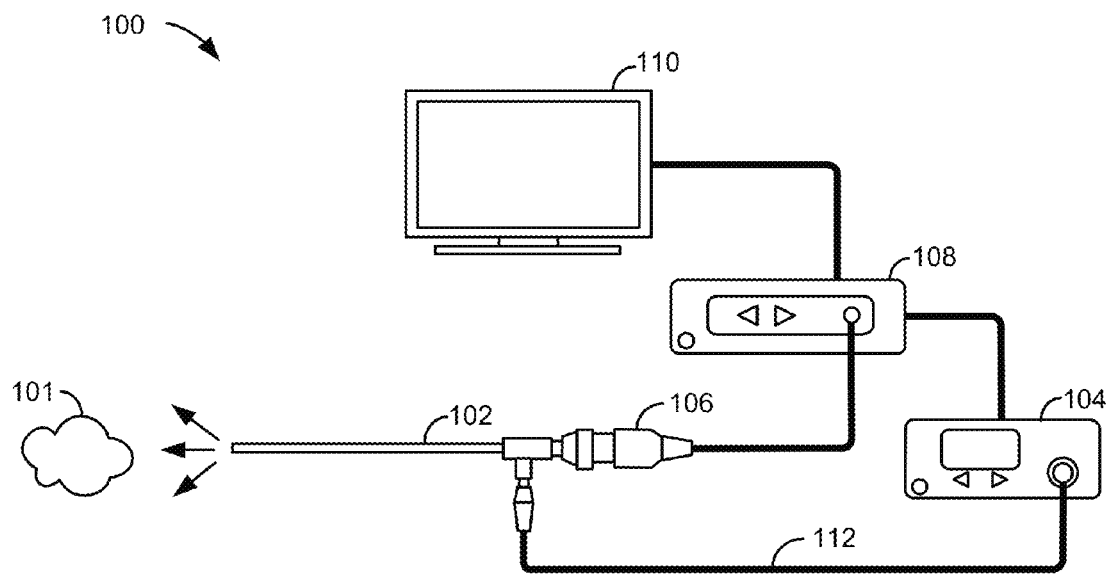
FIG. 1 is a simplified schematic diagram of an endoscope system for concurrent imaging in both the visible and NIR regions according to an embodiment of the present invention.

FIG. 1 is a simplified schematic diagram of an endoscope system for concurrent imaging in both the visible and NIR regions according to an embodiment of the present invention. The basic schematic block diagram of an endoscope system for simultaneous or concurrent imaging in both visible and NIR regions as illustrated in FIG. 1 is exemplary and not intended to limit the present invention. A number of embodiments of the present invention that include illumination through an endoscope with both visible and NIR light at the same time are included within the scope of the invention.

The endoscope system 100 includes an endoscope 102, a light source 104, a camera 106, a controller 108, a monitor 110 and a light guide 112. The endoscope 102 provides a wide transmission band over the visible and NIR spectrum with small chromatic aberration between the wavelengths in the visible and NIR spectrum. The light source 104, described more fully below, generates visible light (e.g., 400 nm-700 nm, in particular 420 nm-680 nm) as well as NIR excitation light with wavelengths in a first NIR spectrum (e.g., 790 nm-820 nm, in particular in the vicinity around 800 nm). The light source 104 can be operated in different modes depending on the imaging modes. As described more fully below, the light source is operable to output both NIR light and visible light, with independent control over each of the wavelength regions. For example, the light source can output NIR light, with no visible output. Alternatively, the light source can output visible light with no NIR light. Additionally, the light source can output both NIR light and visible light concurrently.

The output light from the light source 104 is sent through a light guide 112 into the endoscope 102 to illuminate a target tissue 101 and its surrounding area. In an embodiment, the light guide is an optical fiber cable such as a glass fiber bundle including a plurality of multimode optical fibers, liquid light guides, or the like. The reflected visible light and the excited fluorescence emission with wavelengths in a second NIR spectrum (e.g., 830 nm-900 nm) are received by the endoscope 102 to be imaged by the camera 106. In the exemplary endoscope system 100 illustrated in FIG. 1, the camera 106 is located in the proximal end of the endoscope 102. Light from the target tissue 101 and its surrounding area is transferred through the optical system in the endoscope 102 and then imaged by the camera 106. Although not depicted in the figures, a camera may also be located in the distal end of the endoscope and the light from the target tissue and its surrounding area can be collected and imaged by the camera directly. One of ordinary skill in the art would recognize many variations, modifications, and alternatives.

The controller 108 receives image signals from the camera 106 and processes the image signals for display. The controller 108 is capable of independently adjusting the visible light and the NIR excitation light in the light source 104 using feedback control based on analyzing the image signals, which will be described in detail later. The live image signals captured by the camera 106 and processed by the controller 108 are eventually displayed on the monitor 110.

In some embodiments, multiple fluorescent dyes and multiple excitation wavelengths are utilized, with optical filters (i.e., notch filters) utilized in the imaging optical path that block the excitation light from each of the excitation sources from passing to the detector. An optical filter with multiple notches (e.g. dual notch) having low transmission or multiple single notch optical filters are utilized in these embodiments. Reflected visible light and fluorescent light from the target tissue (at multiple fluorescent wavelengths in the case of multiple fluorescent dies) is transmitted through the optical filter(s) for subsequent detection at the detector. Since the two dyes can have different responses to the excitation light, embodiments provide benefits not available using conventional techniques. In some implementations, the NIR excitation source provides excitation light peaking at multiple wavelengths in order to produce efficient fluorescence from each of the fluorescent dies. Moreover, in some embodiments, the NIR excitation source is controllable to produce light having a single and adjustable excitation peak, multiple excitation peaks, or the like depending on the fluorescent dies that are being utilized during a particular medical procedure.

Embodiments of the present invention provide for concurrent illumination in both the visible and NIR spectrum as well as concurrent imaging of both the visible light reflected from the sample, tissue, or specimen and the fluorescent light emitted by the fluorescent dye, which can be associated with the sample, tissue, or specimen. This concurrent or simultaneous imaging of both visible reflected light and fluorescent emitted light using a single sensor contrasts with conventional systems that utilize time sequential imaging at these differing wavelengths or multiple image sensors for these different wavelengths that utilize an optical system to split the different wavelengths to direct the different wavelength to each of the multiple image sensors.

Figure 2:
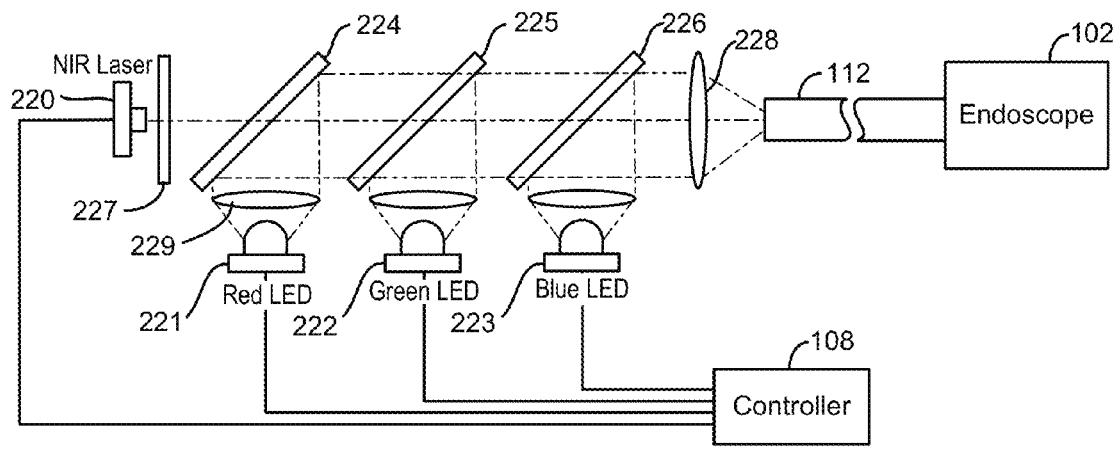
FIG. 2 is a simplified schematic diagram of a first embodiment of a light source for an endoscope according to an embodiment of the present invention.

FIG. 2 is a simplified schematic diagram of a first embodiment of a light source for an endoscope according to an embodiment of the present invention. Referring to FIG. 21, a NIR laser 220 generates excitation light with wavelengths in the first NIR spectrum (e.g., 790 nm-820 nm). In some embodiments, the laser 220 is a semiconductor laser, but other lasers, LEDs, and the like can be utilized. The excitation light from laser 220 passes through laser-line filter 227 that is characterized by a very narrow passband (e.g., 10 nm wide). The laser-line filter 227 transmits the desired excitation wavelengths while suppressing side-band radiation.

In the embodiment illustrated in FIG. 2, a plurality of sources, for example, red LED 221, green LED 222, and blue LED 223 provide light that is used to generate the visible light emission used in the endoscope. Red light from the red LED 221, green light from the green LED 222, and blue light from the blue LED 223 are combined using an appropriate ratio of the light intensity from each source to form white light as described more fully below. The color combiners 224, 225, and 226 combine the light from the NIR laser 20 as well as the light from the red LED 221, green LED 222 and blue LED 223 to form the multi-spectral output that is input into the endoscope 102. As illustrated in FIG. 2, the combined light from the NIR and visible source is coupled by lens 228 into the light guide 112 and then provided to the endoscope 102 for illumination.

The NIR laser 220, red LED 221, green LED 222 and blue LED 223 are each independently controlled by the controller 108. Through the use of the controller, the intensity of the NIR excitation light and the intensity of the visible light can be adjusted, for example, by changing the driving current provided to the NIR laser and the LEDs. In the fluorescence imaging mode, as described more fully below, the intensity of the visible light is adjusted (e.g., attenuated) in order to achieve the desired contrast between the fluorescence image and the visible light image. Additional optical approaches, such as the use of neutral density filters, or electrical approaches, such as modulation methods, can be applied to attenuate the visible light significantly and/or adjust the light intensity with the desired precision.

Figure 3:
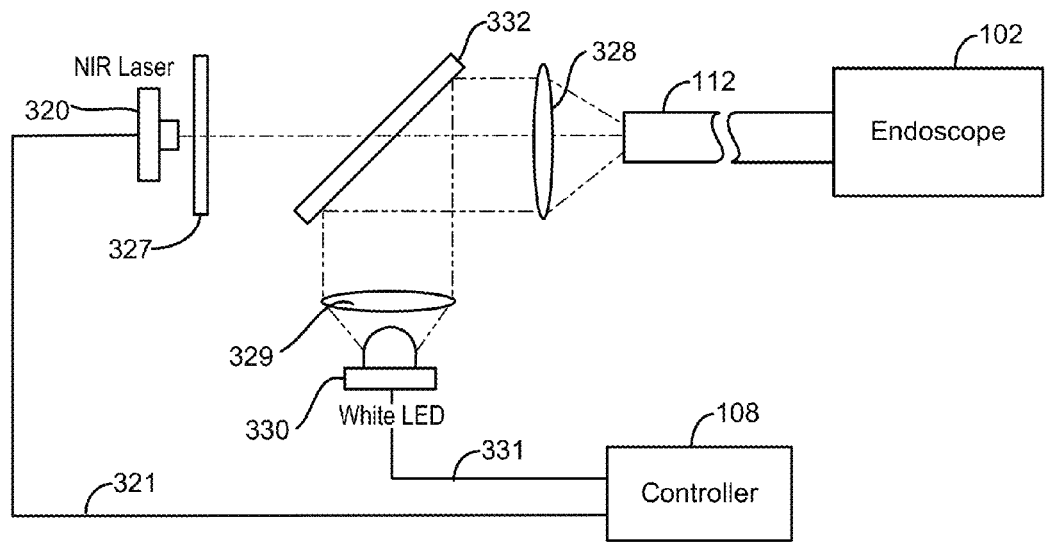
FIG. 3 is a simplified schematic diagram of a second embodiment of a light source for an endoscope according to an embodiment of the present invention.

FIG. 3 is a simplified schematic diagram of a second embodiment of a light source for an endoscope according to an embodiment of the present invention. In the alternative embodiment illustrated in FIG. 3, a NIR laser 320 generates excitation light with wavelengths in the NIR spectrum (e.g., 790 nm-820 nm). In a manner similar to FIG. 2, laser-line filter 327, which is characterized by a narrow passband (e.g., 10 nm), is utilized to transmit the desired excitation wavelengths while suppressing side-band radiation. A white LED 330, for example. including a blue or UV LED with a phosphor coating, is used to generate visible light with wavelengths from 400 nm to 700 nm. A color combiner 332 combines the NIR excitation light from the NIR laser 320 with the visible light from the white LED 330. The combined light is coupled into the light guide 112 and sent to the endoscope 102 for illumination.

As discussed in relation to FIG. 2, the NIR laser 320 and the white LED 330 can be independently controlled by the controller 108 as represented by control lines 321 and 331. The intensity of the NIR excitation light and the intensity of the visible light can be adjusted by changing the driving current of the laser and LED or by other methods. In the fluorescence imaging mode, as described more fully below, the intensity of the visible light is adjusted (e.g., attenuated) in order to achieve the desired contrast between the fluorescence image and the visible light image. Additional optical approaches, such as the use of neutral density filters, or electrical approaches, such as modulation methods, can be applied to attenuate the visible light significantly and/or adjust the light intensity with the desired precision.

Figure 4:
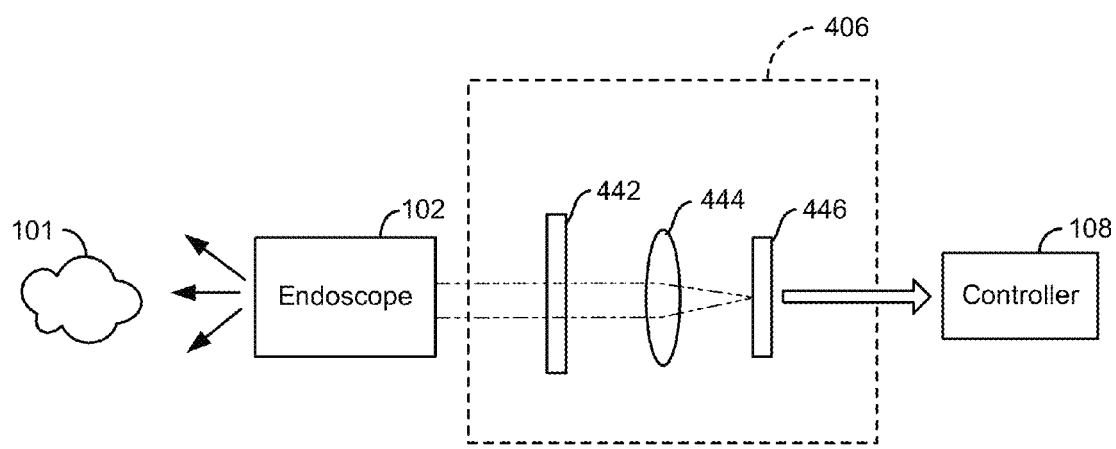
FIG. 4 is a simplified schematic diagram illustrating an optical system of a camera according to an embodiment of the present invention.

FIG. 4 is a simplified schematic diagram illustrating an optical system of a camera according to an embodiment of the present invention. The camera 406 includes an excitation light blocking filter 442 (e.g., a notch filter or a dual notch filter for multiple dye applications), imaging optics 444, and image sensor 446. The excitation light blocking filter 442 is a notch optical filter that provides a blocking band in the NIR spectral range associated with excitation light (e.g., 790 nm to 820 nm for ICG dye) and a transmission band in the visible (e.g., 400 nm-700 nm) and the NIR spectral range associated with the fluorescence emission (e.g., 830 nm-900 nm). Using this optical system, the reflected visible light and the fluorescence emission both pass through the excitation light blocking filter 442 and can be imaged by the camera. The NIR excitation light that is reflected from the tissue and surrounding areas is blocked by the excitation light blocking filter. The imaging optics 44 can be one or several optical lenses. The imaging optics 444 collect the light from the endoscope 102 and focuses the collected light on the image sensor 446 to form an optical image. The image sensor can be either CCD or CMOS image sensor as well as other suitable image sensors that are capable of converting an optical image into an electrical signal. The electrical signal is transmitted to the controller 108 for image processing.

Figure 5A:
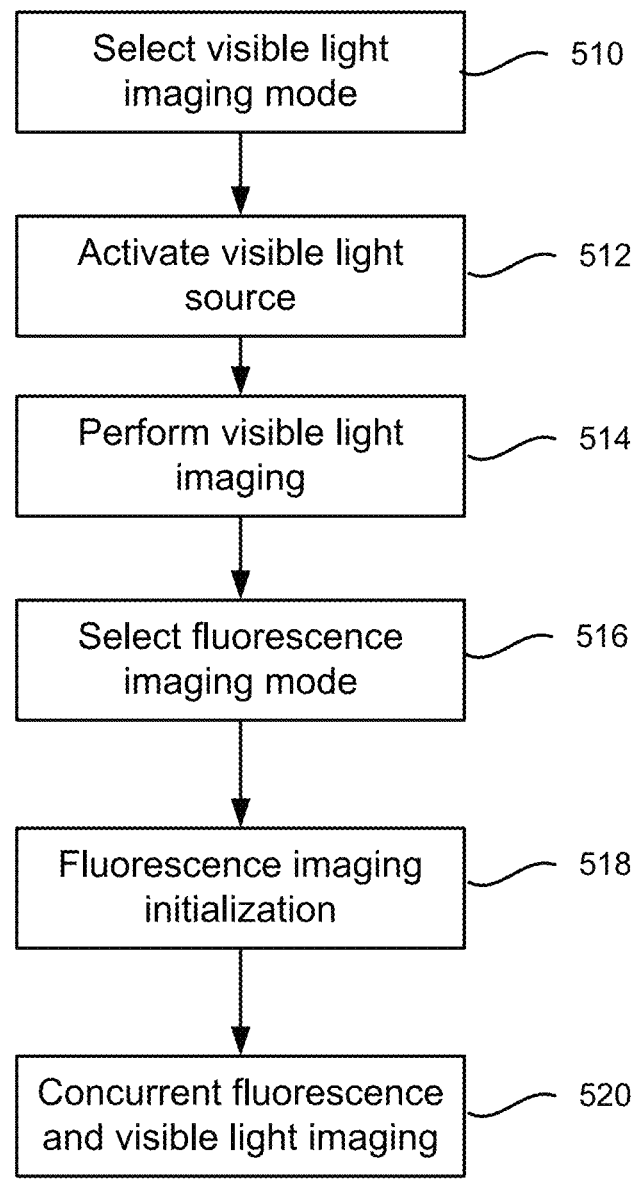
FIG. 5A is a simplified flowchart illustrating a method of operating an endoscope with concurrent imaging according to an embodiment of the present invention.

FIG. 5A is a simplified flowchart illustrating a method of operating an endoscope with concurrent imaging according to an embodiment of the present invention. Because embodiments of the present invention image both visible reflected light and fluorescent emitted light concurrently or simultaneously, the systems described herein balance the fluorescent emission and resulting image with the visible reflection and resulting image to provide a suitable contrast in the image.

As an example, the endoscopy system illustrated in FIG. 1 can use the steps illustrated in FIG. 5A in a surgical procedure. The visible light imaging mode is selected (510) and can be utilized for the majority of the duration of the procedure. When the visible light imaging mode is selected, the visible light source is activated or turned on (512) and visible light imaging is performed to capture visible light images for display (514). In some embodiments, the NIR source is turned off during the visible light imaging mode, with only the visible light source being used during the visible light imaging mode. In other embodiments, the fluorescent excitation source is turned on, but blocked by a spectral filter or other method to reduce the images resulting from fluorescent emission to a low level in comparison to the visible light imaging.

During operation in the visible light imaging mode, the NIR excitation light is typically in the off condition or is switched off. The visible light, either generated from combining the red, green, and blue LEDs as discussed in relation to FIG. 2 or generated from the white light LED illustrated in FIG. 3, is switched or turned on as a result of activation of the visible light imaging mode. In some implementations, the visible light imaging mode is a default mode and the visible light imaging mode is activated when the endoscopy system is initially turned on. The visible light is guided into the endoscope 102 illustrated in FIG. 1 via the light guide 112 to illuminate the target tissue 101 and its surrounding area. The reflected visible light is collected and imaged by the camera 106.

The controller 108 receives and processes the electrical signal associated with the visible light image. The monitor 110 displays the visible light image for use by the system operator, including medical personnel. In some embodiments, the controller can adjust the light intensity automatically based on the received electrical signal associated with the visible light image. In an embodiment, the adjustment by the controller is based on calculating the maximum and average signal values of the image sensor pixels. In this embodiment, the controller adjusts the intensity of the visible light source so that the maximum signal value does not exceed the saturation value of the image sensor while the average signal value is maintained above a predetermined threshold value to provide sufficient light intensity during operation. This adjustment process can be performed manually or automatically depending on the particular implementation. One of ordinary skill in the art would recognize many variations, modifications, and alternatives.

When fluorescence imaging is desired, the fluorescence imaging mode is selected (516). In response to selection of this mode, the system begins an initialization process to determine the intensity of NIR excitation light and the intensity of visible light (518). Additional description related to the initialization process is provided in relation to FIG. 5B described below. After initialization, both fluorescence imaging and visible light imaging are performed concurrently, enabling concurrent or simultaneous display of both fluorescence and visible images of the tissues.

Figure 5B:
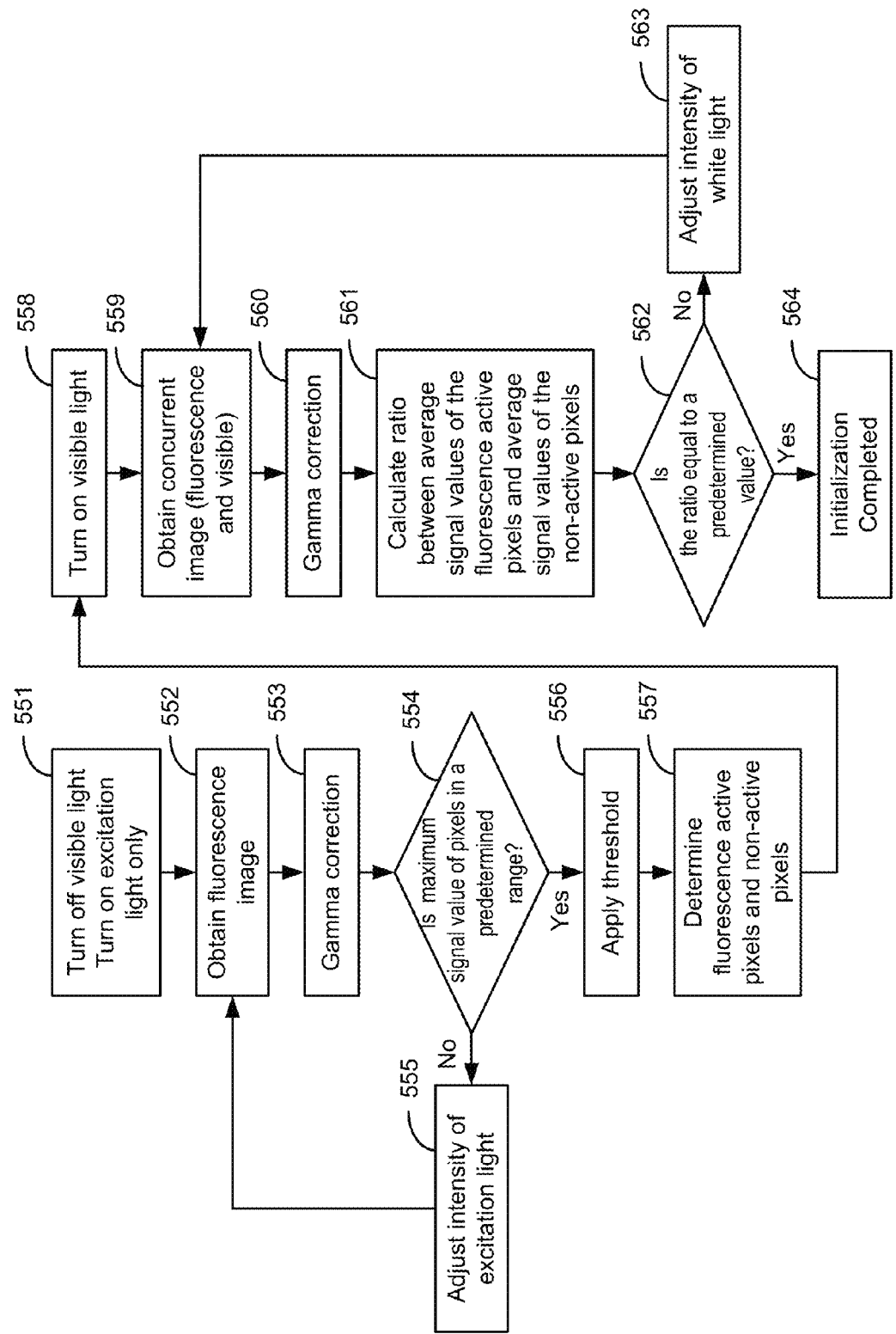
FIG. 5B is a simplified flowchart illustrating a method of initializing a concurrent imaging endoscope according to an embodiment of the present invention.

FIG. 5B is a simplified flowchart illustrating a method of initializing a concurrent imaging endoscope according to an embodiment of the present invention. The method discussed in relation to FIG. 5B illustrates the initial process that is used to achieve the fluorescence imaging mode in the presence of a visible light background image. When the fluorescence imaging mode is selected, the controller will start with an initialization process as illustrated in FIG. 5B.

First, the NIR excitation light is switched on and the visible light is switched off (551). At this stage, only the NIR excitation light from the NIR laser source illuminates the target tissue, generating fluorescent emission. The camera obtains the fluorescence image (552) and sends the electrical image signal to the controller. The processor in the controller applies gamma correction (553) to the received fluorescence image so that the digitized image is a linear function of the luminance. After gamma correction, the processor is utilized to determine if the maximum signal value of the pixels in the fluorescence image is within a predetermined range (554). In other words, a check is performed of the maximum signal value of the pixels in the fluorescent image.

According to embodiments, the maximum signal value is allowed to be within the predetermined range. The upper limit of this predetermined range is utilized to prevent saturation due to too much illumination. As described below, since the visible light will be utilized added in later, the upper limit of the predetermined range is selected such that signal value space is reserved to account for the increase in the signal value associated with the reflected visible light. The lower limit of the predetermined range is utilized to provide a level at which the fluorescence image has adequate brightness for observation and diagnosis.

If the maximum signal value is outside the predetermined range, then adjustments are made to the intensity of the NIR excitation light (555). If the maximum signal value is larger than the predetermined range, the controller will decrease the intensity of the NIR excitation light. If the maximum signal value is smaller than the predetermined range, the controller will increase the intensity of the NIR excitation light. The method repeats processes 552, 553, 554, and 555 as needed until the maximum signal value of the fluorescence image is within the predetermined range.

After the signal is in the predetermined range, a threshold is applied to the fluorescent image (556). The threshold applied to the fluorescence image results in the selection of only pixels with signal values above the threshold as fluorescence active pixels (557). In the embodiments described herein, fluorescence active pixels are pixels for which fluorescence emission is detected for these pixels. The other pixels that have an image intensity less than the threshold are determined to be fluorescence non-active pixels, i.e., pixels for which fluorescence emission is associated. In this way, the fluorescence active pixels are associated with the target tissue and the fluorescence non-active pixels are associated with the surrounding area, which can now be distinguished in the image.

After the NIR excitation light is adjusted to a suitable intensity as described above, the visible light is switched on, but attenuated to one of a plurality of low intensities (558). The attenuation of the visible light is utilized since, for different types of surgical procedures, the intensity of the fluorescent emission varies. Accordingly, the visible light is attenuated to different intensity levels depending on the surgical procedure. Based on experimental or empirical data, the typical intensity level of either the fluorescent excitation light, the visible light, or both for different surgical procedures can be stored and preset in the controller. Once the type of surgical procedure is selected, the controller will attenuate the visible light to this typical intensity level in process 558.

With the combined NIR excitation light and visible light illumination, the camera captures an image that includes both fluorescent emission and reflected visible light (559).

The processor in the controller applies gamma correction to this image (560). The processor then calculates the average signal value of the fluorescence active pixels and the average signal value of the fluorescence non-active pixels. The processor also calculates the ratio between the average signal value of the fluorescence active pixels and the average signal value of the fluorescence non-active pixels (561). The calculated ratio is then compared to a predetermined value (562) and the controller adjusts the intensity of the visible light based on the results of the comparison (563). In other embodiments, rather than using the average value, other statistical measures, including maximum and minimum values, median values, one or more standard deviations around the mean, or the like are utilized to characterize the signal value of the fluorescence active pixels and the fluorescence non-active pixels.

If the calculated ratio is higher than the predetermined value, the brightness in the non-fluorescence surrounding area is not sufficient and the controller will increase the intensity of the visible light. If the calculated ratio is lower than the predetermined value, the brightness of the non-fluorescence surrounding area is too high and the controller will decrease the intensity of the visible light. Processes 559-563 are repeated until the visible light intensity is adjusted to an appropriate level such that the calculated ratio is equal to the predetermined value. Once the ration is equal to the predetermined value, the initialization process is complete (564).

The initialization process described in relation to FIG. 5B provides a process in which the controller uses the image signals in a feedback loop to control the NIR excitation light and the visible light individually until a sufficient contrast is achieved between the fluorescence image of the target tissue and the visible light image of the non-fluorescence surrounding area.

Figure 6A:
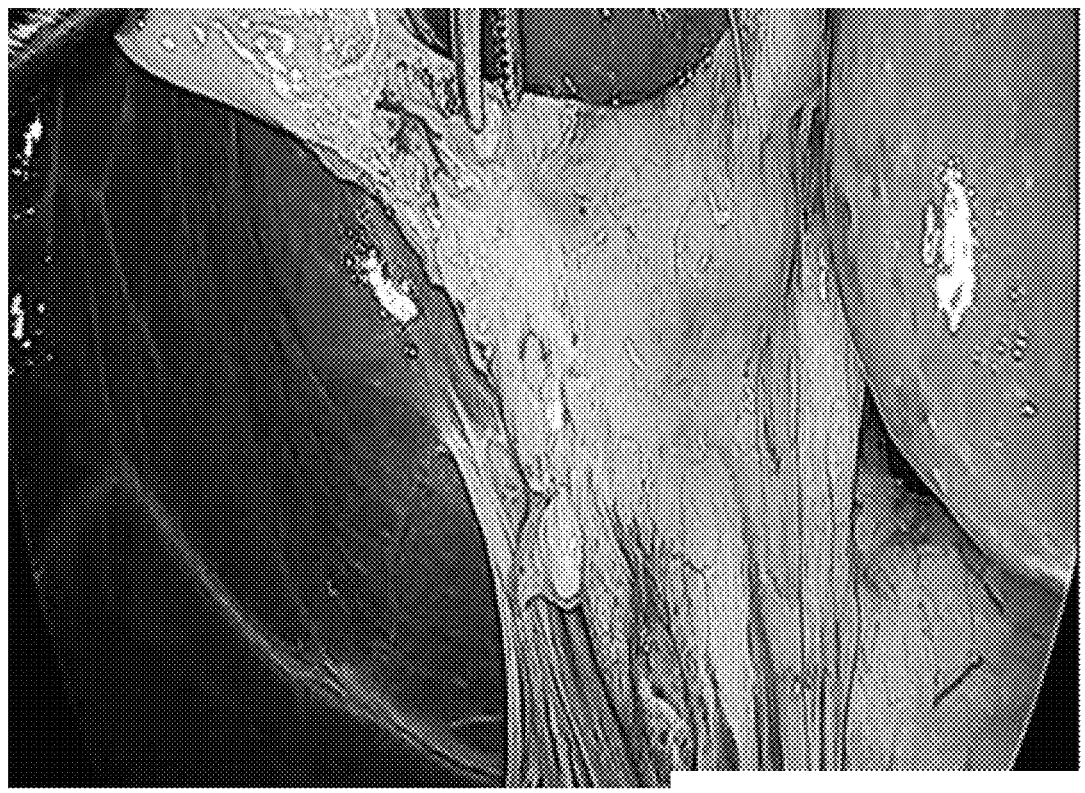
FIG. 6A is a visible light image of a field of view according to an embodiment of the present invention.

FIG. 6A is a visible light image of a field of view according to an embodiment of the present invention. In FIG. 6A, a tissue sample that has been treated by a fluorescent dye, such as ICG, is imaged. Only a part of the tissue is labeled by the fluorescent dye. In FIG. 6A, which is provided to illustrate an environment in which embodiments of the present invention are applicable, imaging is in the visible spectrum with a bright visible source that illuminates the tissue sample. No fluorescent excitation source is utilized and no fluorescent emission is observed in this image.

Figure 6B:
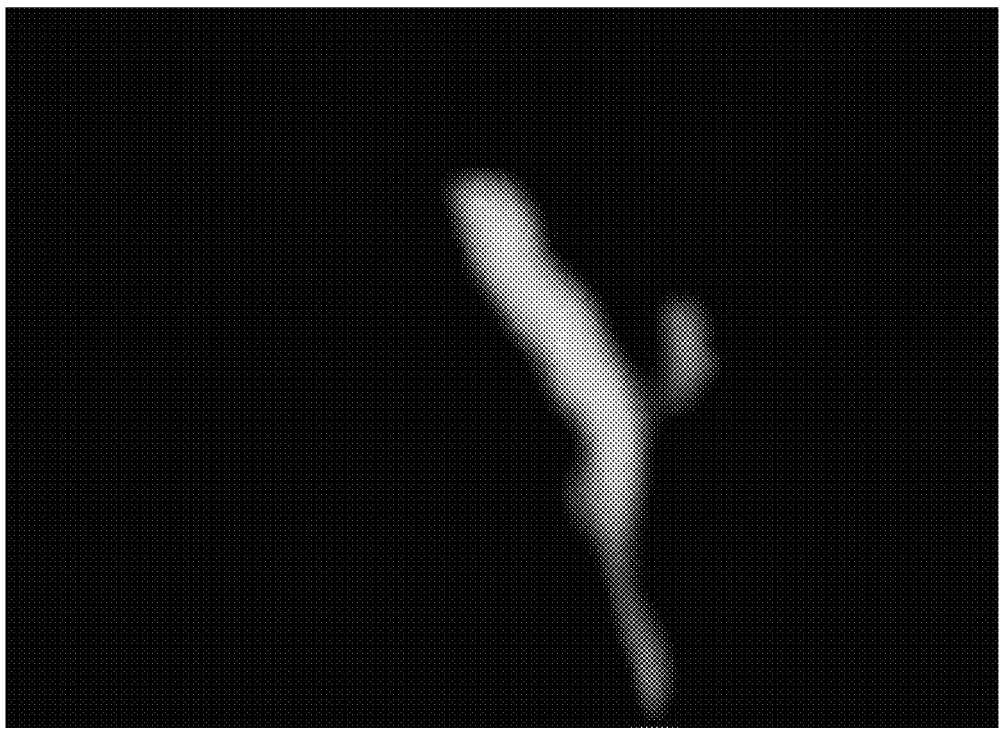
FIG. 6B is a fluorescence image of the field of view illustrated in FIG. 6A.

FIG. 6B is a fluorescence image of the field of view illustrated in FIG. 6A. In the fluorescence image illustrated in FIG. 6B, a fluorescence excitation source is utilized with no visible light illumination. Because the tissue sample has been treated by the fluorescent dye, the section with the fluorescent label is visible in the image as a result of the NIR excitation light and the resulting fluorescence. Referring to FIG. 5B, the fluorescence image illustrated in FIG. 6B corresponds to the fluorescence image obtained in process 552. No substantial visible background is present in this fluorescence image. As discussed in relation to FIG. 5B, once the maximum pixel values are within a predetermined range, it is possible to apply a threshold to the image pixels and determine which pixels are fluorescence active pixels and which are non-active pixels.

Figure 6C:
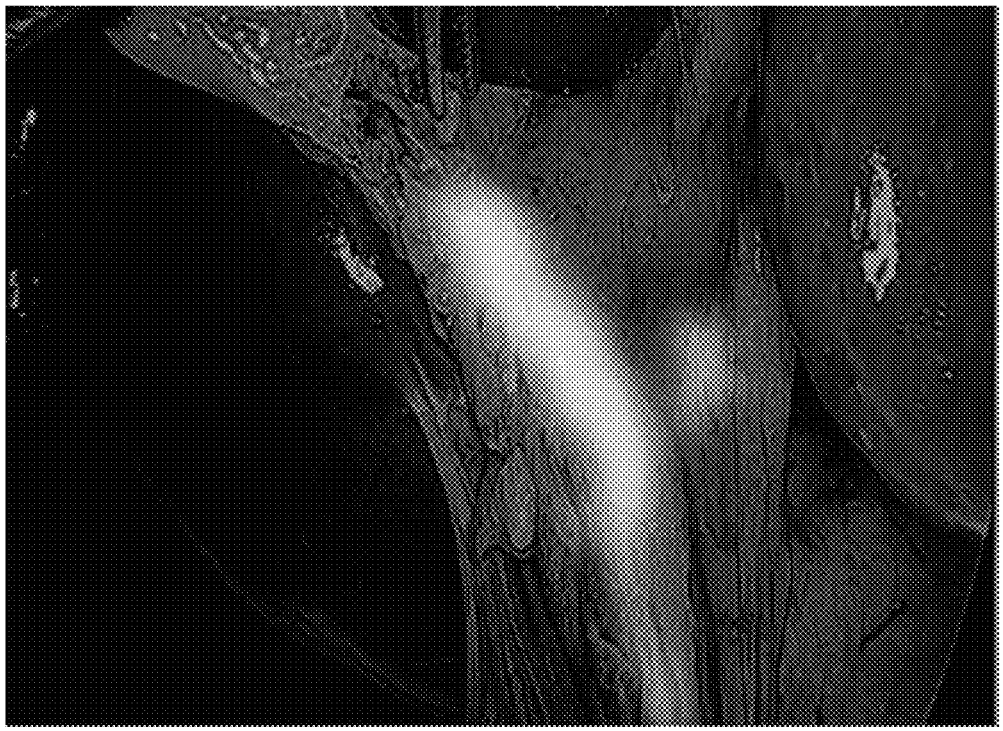
FIG. 6C is a concurrent image including both fluorescent emission and visible reflection according to an embodiment of the present invention.

FIG. 6C is a concurrent image including both fluorescent emission and visible reflection according to an embodiment of the present invention. In the image illustrated in FIG. 6C, fluorescent excitation light is utilized along with low intensity visible light as discussed in relation to process 559. The image associated with the fluorescent label is slightly brighter than that illustrated in FIG. 6B since the fluorescent emission is imaged as well as the visible light reflection from the tissue surface. Because the fluorescent emission was within the predetermined range (process 554), the addition of the visible reflection does not result in saturation of the image in some cases. After initialization, the fluorescence image and the visible light background are imaged to provide information on the fluorescence as well as a visible background to enable useful image capture.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An endoscope system for concurrently imaging at both visible and NIR wavelengths, the endoscope system comprising:
   an endoscope operable to transmit both visible and NIR wavelengths;
   a light source operable to generate visible light and NIR excitation light, wherein an intensity of the visible light is independent from an intensity of the NIR excitation light;
   a camera having a single image sensor operable to concurrently image at both the visible and NIR wavelengths;
   a controller coupled to the visible light and the NIR excitation light; and
   a display device.

2. The endoscope system of claim 1 wherein the controller is operable to independently vary the intensity of the visible light and the intensity of the NIR excitation light.

3. The endoscope system of claim 1 wherein the camera includes an optical filter that blocks the excitation light and passes visible light and fluorescence emission.

4. The endoscope system of claim 1 wherein the light source comprises a plurality of independently controllable solid state light sources.

5. The endoscope system of claim 1 wherein the controller comprises at least one of an electrical attenuator or an optical attenuator.

6. A method of operating an endoscopy system, the method comprising:
   concurrently illuminating a tissue with NIR excitation light and visible light;
   concurrently imaging the tissue at both NIR and visible wavelengths using a single detector; and
   independently adjusting an intensity of the NIR excitation light and an intensity of the visible light.

7. The method of claim 6 wherein at least a portion of the tissue is exposed to a fluorescent dye.

8. The method of claim 6 wherein the NIR excitation light is provided by a NIR laser and the visible light is provided by a solid state white light emitter.

9. The method of claim 8 wherein the solid state white light emitter comprises a plurality of independently controllable solid state light sources.

10. The method of claim 6 wherein concurrently imaging the tissue at both NIR and visible wavelengths using a single detector comprises concurrently imaging fluorescent emission from the tissue and visible light reflected from the tissue.

11. The method of claim 6 wherein independently adjusting the intensity of the NIR excitation light and the intensity of the visible light is performed by a controller coupled to the single detector.

12. A method of initializing an endoscope, the method comprising:

illuminating tissue with NIR excitation light;

imaging fluorescent emission from the tissue with a single image sensor to provide a fluorescence image;

adjusting an intensity of the NIR excitation light until a fluorescence image intensity of the fluorescence image is within a predetermined rage;

determining fluorescence active pixels and fluorescence non-active pixels of the fluorescence image;

illuminating the tissue with visible light;

imaging both the fluorescent emission from the tissue and reflected visible light with the single image sensor;

computing a ratio between an average signal value of the fluorescence active pixels and the fluorescence non-active pixels; and adjusting an intensity of the visible light.

13. The method of claim 12 wherein illuminating tissue with NIR excitation light is substantially free of visible light illumination.

14. The method of claim 12 wherein the endoscope is operable to concurrently image visible light and fluorescent emitted light using the single image sensor.

15. The method of claim 12 wherein determining fluorescence active pixels and fluorescence non-active pixels of the fluorescence image comprises applying a threshold to the fluorescence image obtained by illuminating tissue with the NIR excitation light.

16. The method of claim 12 wherein illuminating the tissue with visible light comprises concurrently illuminating the tissue with the NIR excitation light and the visible light.

17. The method of claim 12 wherein the visible light used to illuminate the tissue with visible light is characterized by an illumination intensity and the visible light after adjusting the intensity of the visible light is characterized by an adjusted intensity greater than the illumination intensity.

18. The method of claim 12 wherein a contrast between the fluorescent emission and the reflected visible light has a first value before adjusting the intensity of the visible light and a second value after adjusting the intensity of the visible light.

* * * * *